United States Patent [19]

Terbot et al.

[11] Patent Number: 5,173,455

[45] Date of Patent: Dec. 22, 1992

[54] LOW SINTERING CORDIERITE POWDER COMPOSITION

[75] Inventors: John F. Terbot, Mobile, Ala.; Richard F. Hill, Chagrin Falls, Ohio

[73] Assignee: Union Carbide Coatings Service Technology Corporation, Danbury, Conn.

[21] Appl. No.: 696,087

[22] Filed: May 6, 1991

Related U.S. Application Data

[62] Division of Ser. No. 321,214, Mar. 3, 1989, which is a division of Ser. No. 911,221, Sep. 24, 1986, Pat. No. 4,835,298.

[51] Int. Cl.⁵ .................... C03C 3/00; C03C 10/08
[52] U.S. Cl. ........................................ 501/12; 501/119
[58] Field of Search ............... 501/9, 7, 12, 69, 119, 501/153, 154; 423/328, 329, 331, 333

[56] References Cited

U.S. PATENT DOCUMENTS

| | | | |
|---|---|---|---|
| 3,761,500 | 9/1973 | Thomas | 260/448 |
| 3,791,808 | 2/1974 | Thomas | 65/30 |
| 3,920,713 | 11/1975 | Feichtinger | 556/182 |
| 4,266,978 | 5/1981 | Prochazka | 106/395 |
| 4,413,061 | 11/1983 | Kumar | 501/7 |
| 4,888,314 | 12/1989 | Bernier et al. | 501/119 |

OTHER PUBLICATIONS

New Routes to Multicomponent Oxide Glasses by Dislich, Angewandte, Chemie, International Edition, vol. 10, No. 6, Jun. 1971, pp. 363–434.

Primary Examiner—Mark L. Bell
Assistant Examiner—Alan Wright
Attorney, Agent, or Firm—E. Lieberstein

[57] ABSTRACT

A Group IIA metal-Group IIIA metal-silicon substantially homogeneous liquid alkoxide is prepared from a reaction mixture of a Group IIA metal, a Group IIIA metal, a silicon tetraalkoxide, and a liquid defined by the formula ROR' where R is an alkyl group and R' is hydrogen or an alkyl group. The alkoxide can then be hydrolyzed, azeotropically distilled, dried, milled, and calcined to produce a ceramic powder. Advantageously, the ceramic powder can be compacted and sintered at relatively low temperatures which enable it to be used in electrical applications where high sintering temperatures would be deleterious.

3 Claims, 2 Drawing Sheets

LOW SINTERING CORDIERITE POWDER COMPOSITION

This application is a division of prior U.S. Ser. No. 321,214, filing date Mar. 3, 1989 which is a allowed division of U.S. Ser. No. 911,221 filed on Sep. 24, 1986 now U.S. Pat. No. 4,835,298.

BACKGROUND OF THE INVENTION

Alumina, mullite, and other refractory ceramics have been used for some time as substrates for printed circuits having conduction patterns made from inks or pastes containing tungsten, molybdenum, gold, silver, or copper powders, terminal pads to attach semiconductor chips, connecting leads, capacitors, resistors, covers, and vias (i.e. holes filled with metal paste) to connect different layers of conductive patterns. Alumina is preferable due to its excellent electrical insulating properties, thermal conductivity, stability, and strength. However, this material has some disadvantages including signal propagation delay and noise in high performance applications, restriction of the type of the conductive metals due to alumina's high maturation temperature, and a high thermal expansion coefficient.

As an alternative to alumina, U.S. Pat. No. 2,920,971 to Stookey discloses the use of glass ceramics with dielectric properties and high mechanical strengths. Stookey's glass ceramics are characterized as "bulk-crystallized" or "bulk" glass ceramics as opposed to sintered glass ceramics. Bulk glass ceramics are generally inferior to sintered glass ceramics due to the latter's high flexural strength.

Although sintered glass ceramics are well known, they are generally unsuitable as substrates for printed circuits, because many glass ceramics can only be sintered at temperatures well in excess of 1000° C. Such temperatures are above the melting point of the gold (having a melting point of 1064° C.), silver (962° C.), and copper (1083° C.) conductors within the printed circuit.

U.S. Pat. No. 4,587,067 to Agrawal et al. discloses a method of manufacturing low thermal expansion-modified cordierite compositions. The process comprises: Blending MgO, $Al_2O_3$, $SiO_2$, and $GeO_2$; Homogenizing the blended material by wet ball milling; Oven drying; Comminuting; Cold compacting; Sintering; and Consolidation to full density. Sintering is carried out at about 1350° C.

One way of sintering below 1000° C. is by treating the glass powder with an alkali solution and then sintering under vacuum, as taught by Helgesson, *Science of Ceramics*, British Ceramic Society, 1976, pp. 347-361. Another technique of sintering below 1000° C. is to use glass compositions which are unsuitable as substrates for printed circuits due to their relatively high fluidity. This fluidity causes movement of the substrate's conduction patterns when sintering these materials.

U.S. Pat. No. 4,413,061 to Kumar, et al., ("Kumar") seeks to overcome the above-noted problems with respect to sintered glass ceramics by crystallizing the glass ceramics during sintering so that a rigid network of crystallites are formed. These crystallites reduce the fluidity of the substrate, thereby permitting greater dimensional and distortional control. Cordierite ($2MgO.2Al_2O_3.5SiO_2$) glass ceramics according to Kumar are prepared by melting a mixture of $Al_2O_3$, MgO, $SiO_2$, and other materials, quenching the molten glass by pouring it into cold water to produce a cullet, grinding the cullet, mixing the ground cullet with a binder, casting the mixture into sheets, placing conductive patterns on the sheets, laminating, and sintering usually at temperatures of at least 925° C. (see Table III). As to one example (i.e. Example 10), sintering temperatures as low as 870° C. are indicated to be satisfactory. The resulting cordierite is primarily in the μ or α phases or mixtures thereof. Although Kumar produces cordierite, the grains of this cordierite are not homogenous. Kumar also requires a very high temperature glass melting step and a fairly high temperature sintering step. Moreover, it is difficult to achieve uniform fiber reinforcement when the fibers are mixed with Kumar's ceramic powder prior to sintering.

Ceramic materials have been formed from alkoxides. However, it has not been possible to manufacture certain ceramic compositions from a homogeneous liquid magnesium-aluminum-silicon alkoxide in a single reactor, because the magnesium alkoxides are generally insoluble in common organic solvents. Even if each of the alkoxides are separately formed and then mixed, a uniform distribution cannot be achieved due to magnesium's insolubility.

U.S. Pat. Nos. 4,242,271 and 4,288,410 to Weber, Hill, and Weeks prepare aluminum alkoxides by reacting impure aluminum with a stoichiometric excess of monohydric alcohol.

U.S. Pat. No. 3,761,500 to Thomas ("Thomas") discloses a magnesium, aluminum double alkoxide and the process of preparing it according to the following non-catalytic reaction:

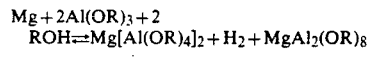

$$Mg + 2Al(OR)_3 + 2 ROH \rightleftharpoons Mg[Al(OR)_4]_2 + H_2 + MgAl_2(OR)_8$$

where the OR group is an alkoxy group of 4-7 carbon atoms. Thomas' process involves the reaction of two equivalents of aluminum alkoxide with one equivalent of magnesium. Consequently, the composition of the final product is limited to a ratio of magnesium to aluminum of 1 to 2. The double alkoxides can be used to form ultra high purity spinel by hydrolyzing the double alkoxide with water and then calcining or firing the hydrolysis product (col. 2, lines 33-41). The product of this process is useful as a refractory material.

U.S. Pat. No. 3,791,808 to Thomas relates to a process of preparing a thermally crystallizable oxide product by hydrolyzing a silicon alkoxide, reacting the hydrolyzed product with a metal alkoxide, an aqueous metal solution, or water to produce a gel, and heating to produce a thermally crystallized product. The thermally crystallized product is preferably a particulate mass with a particle size less than about 0.2 micron which can be treated to produce either a dense or porous body. Although any metal is said to be suitable in the metal oxide component, magnesium cannot be used in the alkoxide form, because such alkoxides are not suitably soluble. The products disclosed by U.S. Pat. No. 3,791,808 are useful in heat exchangers, dinnerware, and filters.

U.S. Pat. No. 4,052,428 to Lerner, et al., relates to the preparation of stable aluminum alkoxide solutions by reacting aluminum metal with a mixture of isobutyl alcohol and n-butyl alcohol. The resulting alkoxide is useful in forming catalysts and paint additives.

U.S. Pat. No. 4,266,978 to Prochazka discloses a non-aqueous gel of at least two metal oxides which are prepared by reacting a metal alkoxide with a metal halide and heating the reaction product. The gel is calcined at a temperature from 600° C. to about 1300° C. to produce a glassy or crystalline submicroscopically homogeneous mixture of the oxides.

U.S. Pat. No. 4,422,965 to Chickering, et al., discloses a process for containing a solution of nuclear waste in borosilicate glass. The glass precursor is prepared from a mixture of alkoxides which are hydrolyzed and then polymerized into an organic-free oxide network.

U.S. Pat. No. 4,430,257 to Pope, et al., relates to a method of containing nuclear waste in a glass forming composition prepared from tetraethylorthosilicate (TEOS), an aluminum alkoxide, or a magnesium-aluminum alkoxide in a 1 to 2 ratio, a boron alkoxide or a calcium alkoxide, an alcohol, and a sodium compound. Once the composition components are intimately mixed, excess alcohol and water are boiled off as an azeotrope to leave a homogeneous colloidal glass forming composition.

SUMMARY OF THE INVENTION

In accordance with the present invention, at least one Group IIA metal (i.e. beryllium, magnesium, calcium, strontium, barium, and radium), at least one Group IIIA metal (i.e. aluminum, gallium, indium, and thallium), and at least one silicon tetraalkoxide (e.g. tetraethylorthosilicate, tetramethylsilicate) are used to produce a Group IIA metal-Group IIIA metal-silicon mixed liquid alkoxide which is converted to a ceramic powder and can then be compacted and sintered. In a preferred embodiment, the compacted and sintered ceramic powder is cordierite, the Group IIA metal is magnesium, the Group IIIA metal is aluminum, the silicon tetraalkoxide is tetraethylorthosilicate, and the Group IIA metal-Group IIIA metal-silicon mixed liquid alkoxide is magnesium-aluminum-silicon ethoxide.

A homogeneous, soluble, liquid alkoxide is prepared by reacting a mixture of at least one silicon tetraalkoxide, at least one Group IIA metal, and at least one Group IIIA metal with a liquid defined by the formula ROR' where R is an alkyl group and R' is hydrogen or an alkyl group. R is preferably a lower alkyl group with 1 to 3 carbon atoms, while R' is preferably hydrogen. The liquid defined by the formula ROR' can be, inter alia, an alcohol or an ether provided that the liquid will remain a liquid under alkoxide synthesis conditions (i.e. pressure and temperatures). As noted supra, the preferred alkoxide, is magnesium-aluminum-silicon liquid ethoxide which results when the liquid defined by the formula ROR' is ethanol. When ethanol is utilized, its reaction with the metals results in the generation of hydrogen whereas no gas is generated by the reaction if an ether is used instead.

The silicon tetraalkoxide can be formed from any lower alkyl group with alkyl groups of 1 to 3 carbon atoms being most preferred. It is particularly preferred that the liquid defined by the formula ROR' and the silicon tetraalkoxide have the same ligand. In the preferred embodiment, this is achieved by utilizing tetraethylorthosilicate as the silicon tetraalkoxide and by using ethanol as the liquid defined by the formula ROR'.

During the reaction of the Group IIA metal, the Group IIIA metal, and the silicon tetraalkoxide, less than the stoichiometric amount of liquid defined by the formula ROR' is initially used and additional quantities of this liquid are periodically added to the reaction mixture to control the reaction rate, and such addition is continued until the reaction is completed. When the liquid defined by the formula ROR' is ethanol, this liquid is added when the reaction's rate of hydrogen generation ceases or substantially ceases. The reaction mixture can optionally contain a rate enhancement agent in an amount effective to increase the rate of alkoxide synthesis. One example of a suitable rate enhancement agent is any alkoxylation catalyst such as, molecular halogens, metal halides, and mixtures thereof. Preferably, the rate enhancement agent is molecular iodine in an amount of $5.5 \times 10^{-4}$ to $1.3 \times 10^{-3}$ moles per mole of Group IIA metal.

One alternative embodiment is to replace all or part of the at least one Group IIA metal with at least one Group IA metal (i.e. lithium, sodium, potassium, rubidium, cesium, and francium).

It is believed that the magnesium and aluminum in the alkoxide are not merely present as a blend of magnesium alkoxide and aluminum alkoxide, but they are instead complexed during the alkoxylation step. This complex is thought to be carried through to the compacted and sintered cordierite to give it and all the intermediate materials formed by the reaction improved properties. The complex in its alkoxide form is believed to be a homopolar alkoxide of $Mg(OR)_2$ and $Al(OR)_3$ as follows:

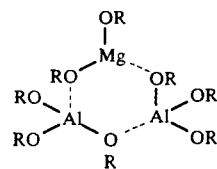

wherein R is an alkyl group. It is when this homopolar alkoxide is formed that magnesium is soluble in ethanol containing aluminum and silicon tetraalkoxide. Such homopolar alkoxide formation may be achieved when the molar ratio of magnesium to aluminum in the mixed liquid alkoxide is between 7.0 to 1 and 0.2 to 1. Thus, molar ratios of magnesium to aluminum of over 1 to 2 which could not be achieved by prior art processes can now be produced.

The mixed liquid alkoxide can be reacted to produce a sinterable, ceramic powder by treating the Group IIA metal-Group IIIA-metal-silicon mixed liquid alkoxide under conditions which produce a hydrated Group IIA metal-Group IIIA metal-silicon mixed oxide and drying the hydrated Group IIA metal-Group IIIA metal-silicon mixed oxide. In the preferred embodiment, the hydrated Group IIA metal-Group IIIA metal-silicon mixed oxide is hydrated magnesium-aluminum-silicon mixed oxide. After this hydrated metal mixed oxide is dried, it can be milled by ball or jet milling. Alternatively, the material can be wet milled in ethanol or water and then dried.

The step of treating the mixed liquid alkoxide to produce a hydrotreated Group IIA metal-Group IIIA metal-silicon mixed liquid oxide is preferably carried out by hydrolyzing the Group IIA metal-Group IIIA metal-silicon mixed liquid alkoxide. Prior to hydrolyzing, the alkoxide is optionally first diluted with ethanol. A solution of water and ethanol is then added to effect hydrolysis. The water is preferably diluted with ethanol at a 1:12 to 1:6 weight ratio of water to ethanol. These ratios can be varied to control the rate of oxide formation.

Specifically, hydrolysis rates are increased by high ratios of water to ethanol and decreased by low ratios of water to ethanol. A fast rate of formation will increase the tendency to yield a dense oxide with many phases in the sintered product, while a slow rate of formation tends to produce a homogeneous oxide with one phase in the sintered product.

Hydrolyzing results in the formation of a product which may be a sol. When permitted to stand, a gel is formed. After gelation, the gel is optionally quiescently aged for a time sufficient to effect substantial polymerization and to complete hydrolysis. Useful polymerization generally occurs in anywhere between 10 seconds and 24 hours, depending upon (amongst other things) the concentration of water. After quiescently aging, water is optionally added to the gel, and the gel mixed with water is agitated to shear the gel and break it up into small particles. This agitation and continued hydrolysis may be at temperatures up to 80° C. for up to 5 days depending on temperature and dilution. After shearing, alcohol produced from the hydrolyzing step is optionally separated from the hydrated Group IIA metal-Group IIIA metal-silicon oxide by azeotropic distillation. The alcohol removed by azeotropic distillation can be further distilled to remove any water and then recycled to the alkoxylation reaction or to the hydrolysis reaction. Such recycling makes the process more economical by reducing the quantity of new ethanol added to the alkoxylation and hydrolysis reactions. In addition, the waste treatment requirements of the process are eliminated. The azeotropic distillation step is, however, optional, because the subsequent step of drying can be used to effect alcohol removal in addition to the removal of water.

It is often desirable to dope the ceramic powder with boron to aid sintering. One way of achieving this result is by blending a solution of boric acid crystals and alcohol with the mixed liquid alkoxide prior to hydrolyzing. The ceramic powder can also be doped with phosphorus to promote nucleation and to regulate microstructural development. One way to effect such doping with phosphorus is by adding a solution of phosphoric acid, water, and ethanol to the liquid alkoxide prior to hydrolyzing. In addition, lithium, titanium, tin, and zirconium oxides similarly can be used to dope the resultant ceramic powder, thereby promoting nucleation or sintering.

After drying and milling, the hydrated Group IIA metal-Group IIIA metal-silicon mixed metal oxide can be calcined (i.e. dehydroxylated) to form a Group IIA metal-Group IIIA metal-silicon mixed metal oxide. In the preferred embodiment, one way to effect calcination is by warming the hydrated magnesium-aluminum-silicon mixed metal oxide to 600°–800° C. One preferred calcination temperature schedule comprises warming the hydrated Group IIA metal-Group IIIA metal-silicon oxide from room temperature to 100° C. over the course of an hour, maintaining the temperature at 100° C. for one hour, heating from 100° C. to 700°–750° C. at a rate of 100° C. per hour, and cooling.

After calcining, the Group IIA metal-Group IIIA metal-silicon mixed metal oxide can be milled by dry ball milling, wet ball milling in ethanol, or jet milling to reduce the particle size of the mixed metal oxide.

In the preferred embodiment, the product of calcination is an agglomerate of adhered, uniformly sized, amorphous primary particles of magnesium-aluminum-silicon oxides. The agglomerate has a uniform, homogeneous composition as a result of being ultimately formed from a homogeneous liquid solution and is generally friable to permit milling by any suitable means, (such as those disclosed in the previous paragraph) to a smaller size and a more uniform size distribution than the cullet of Kumar. When doped with boron or phosphorus, the primary particles may contain oxides of boron and phosphorus. Each of the agglomerates typically has a size ranging from 1 to 50 microns.

After optional calcination, the Group IIA-Group IIIA-silicon mixed oxide powder is milled to render it capable of being compacted and sintered to substantially full density. Sintering causes crystallization of the amorphous primary particles. The threshold sintering temperature is an indication of the homogeneity and consistency of the grains of mixed metal oxides. In the present invention, the magnesium-aluminum-silicon mixed oxide is uniform to the extent that it can be sintered at temperatures less than 925° C., preferably less than 900° C., more preferably less than 875° C., and most preferably at 850° C. which is below the threshold sintering temperatures of Kumar.

By controlling the composition of magnesium, aluminum, and silicon in the oxide, crystalline cordierite ceramics are produced during sintering. Preferably, the oxide contains 10–40% by weight magnesium, 15–40% by weight aluminum, and 40–75% by weight silicon. The composition limits are set on the one hand by the need to ensure that cordierite appears as the major crystalline phase in order to achieve desired thermal expansion coefficients and, on the other hand, to facilitate sintering at low temperatures. If boron or phosphorus doping agents were used, the cordierite also will include oxides of boron and phosphorus, respectively.

While not wishing to be bound by theory, it is believed that the ease with which the agglomerate produced by calcination is ground to a smaller size than that of Kumar's glass cullet, and the ability of the ground agglomerate to be sintered at lower temperatures than in Kumar's process results from the preceeding steps of the present process. Specifically, it is believed that the ease of grinding occurs as a result of the agglomerates being made up of small primary particles. In addition, it may be possible to produce unagglomerated particles. The ability to sinter at low temperatures is achieved due to the high degree of homogeneity resulting from polymerization which occurs during gelling and aging.

DETAILED DESCRIPTION OF THE DRAWINGS

Figure 1:
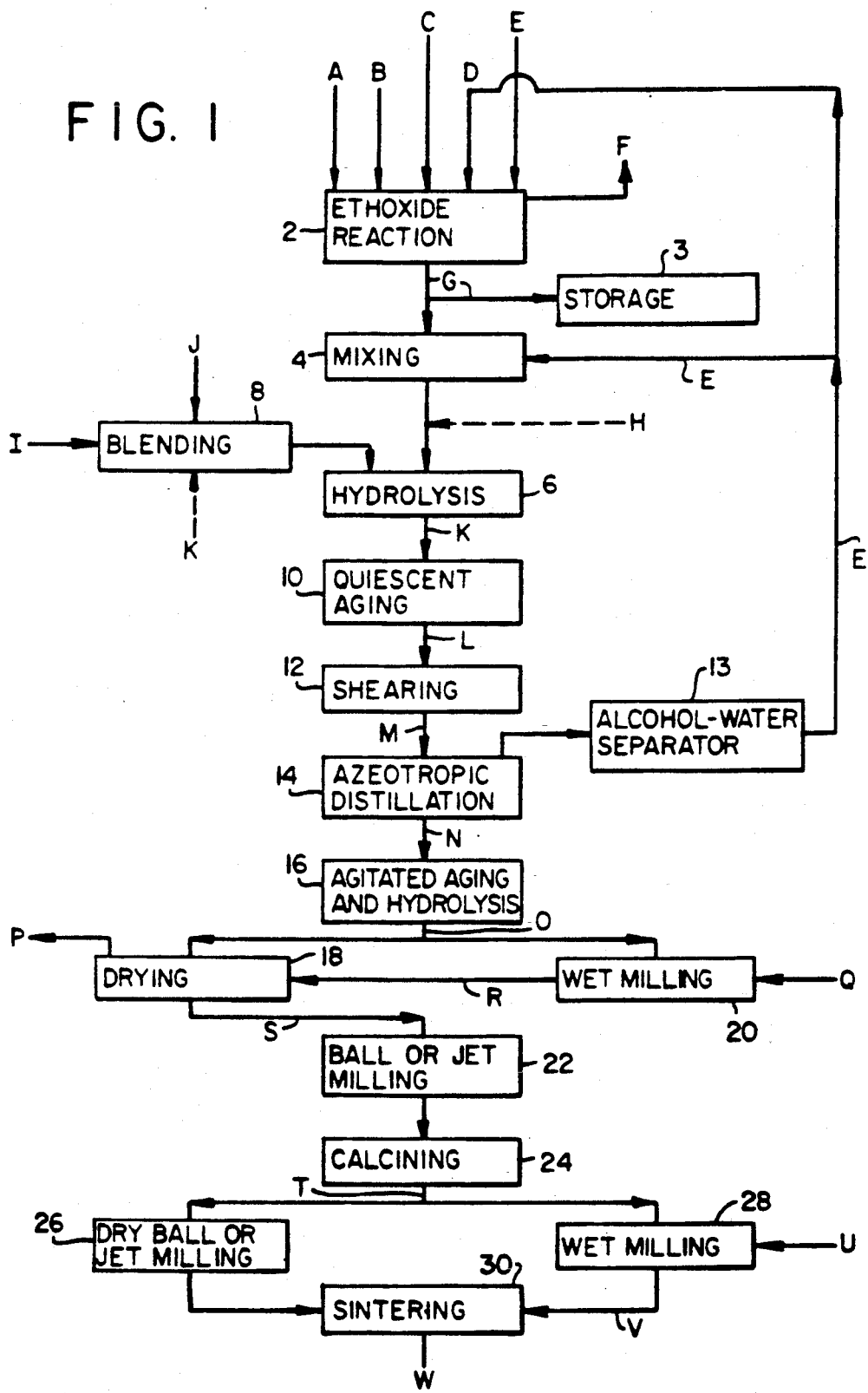
FIG. 1 is a flow diagram depicting the process of the present invention according to the preferred embodiment.

FIG. 1 is a flow diagram showing the process of the present invention according to the preferred embodiment for manufacturing cordierite. In this process, magnesium A, aluminum C, tetraethylorthosilicate E, and ethanol D undergo an ethoxide formation reaction 2 in the presence of an iodine initiator B. The ethoxide formation reaction 2 generates hydrogen gas F and a magnesium-aluminum-silicon mixed liquid ethoxide G which can be either stored 3 or mixed 4 with ethanol E.

Boric acid crystals in ethanol H can optionally be added to the mixture of ethanol and the magnesium-aluminum-silicon mixed liquid ethoxide before the mixture undergoes hydrolysis 6. Hydrolysis 6 is effected by adding a mixture of ethanol I, water J, and optionally phosphoric acid K, all of which have undergone blending 8. Hydrolysis 6 results in the formation of a gel K which is subjected to quiescent aging 10 to effect further polymerization. The aged gel L is then subjected to shearing 12 to break it into a slurry of small particles M, followed by azeotropic distillation 14 which separates ethanol E from the remaining slurry N. The ethanol separated by azeotropic distillation can be recycled to either the mixing step 4 or the ethoxide formation step 2 after drying in alcohol-water separator 13. The slurry N then undergoes optional additional agitation to effect complete hydrolysis 16. The aged gel O is then either subjected to drying 18 which removes water and residual ethanol P or wet milling 20 in the presence of ethanol or water O. After wet milling 20, the milled material R is subjected to drying 18. The dried, hydrated magnesium-aluminum-silicon mixed oxide S can then undergo ball or jet milling 22 followed by calcining 24 to convert the hydrated magnesium-aluminum-silicon mixed oxide to agglomerated magnesium-aluminum-silicon mixed oxide T. The calcined material T then can undergo either dry ball or jet milling 26 or wet milling 28 in ethanol or water U. The milled material V can then be compacted and sintered to produce dense ceramic parts W.

Figure 2:
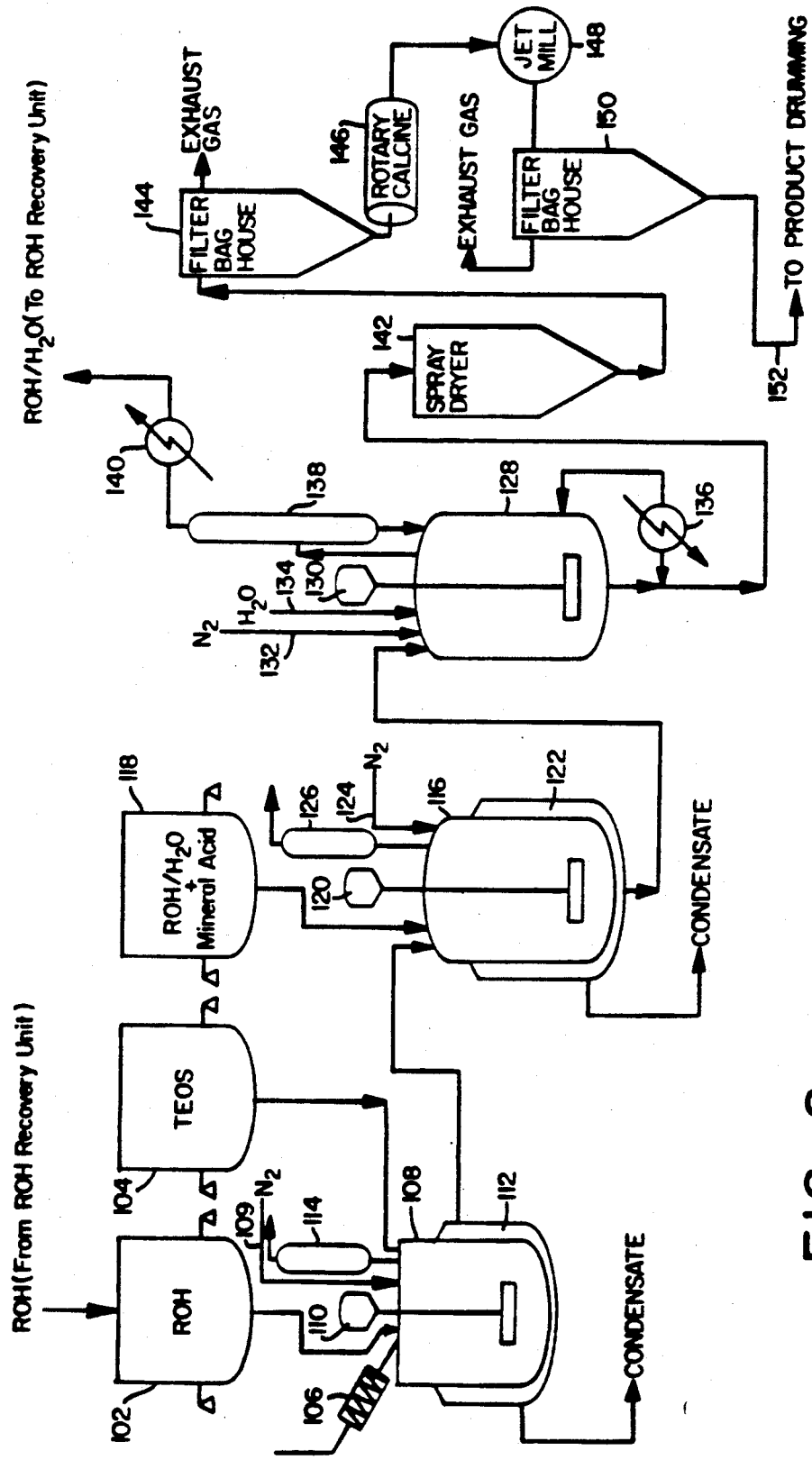
FIG. 2 is a schematic diagram of a commercial version of the present invention according to the preferred embodiment.

FIG. 2 is a schematic diagram of a commercial version of the present invention according to the preferred embodiment. In accordance with this embodiment, alcohol and tetraethylorthosilicate are weighed in alcohol weigh tank 102 and tetraethylorthosilicate weigh tank 104, respectively. Materials from these weigh tanks are charged into alkoxide reactor 108. Magnesium and aluminum are charged to this reactor by screw conveyor 106. In alkoxide reactor 108, the reactants are agitated by mixer 110 and heated by steam jacket 112 surrounding the reactor. Nitrogen from nitrogen source 109 is also added to the alkoxide reactor to prevent formation of an explosive atmosphere during initial charging of reactants. Condenser 114 removes any condensible materials from the vapors leaving the alkoxide reactor 108, so that only non-condensibles (e.g. hydrogen) are withdrawn.

After the alkoxide reaction is completed, the product is withdrawn from the bottom of the alkoxide reactor 108 and charged to hydrolysis reactor 116. Alcohol mixed with water and mineral acid in weigh tank 118 is also charged to hydrolysis reactor 116. The material in this reactor is agitated with mixer 120 and heated by steam jacket 122 to effect hydrolysis. Nitrogen is also added to hydrolysis reactor 116 to prevent explosions. Vapors are removed from the reactor and passed through condenser 126 to return condensible materials to the hydrolysis reactor.

When hydrolysis is completed, the product remains in the hydrolysis reactor 116 to permit quiescent aging and shearing with mixer 120.

After aging and shearing, the material in the hydrolysis reactor 116 is charged to stripper 128 where this material is agitated by mixer 130 and heated by reboiler 136. Nitrogen from nitrogen source 132 and water from water source 134 are added to the stripper to prevent explosions and to provide water for stripping, respectively. Vapors generated in the stripper 128 are withdrawn and passed through azeotropic distillation column 138. Such azeotropic distillation conventionally requires more than one distillation column. Consequently, column 138 represents the plurality of columns needed to effect such azeotropic distillation. The overhead product is passed through condenser 140 to an alcohol recovery system. The bottom product from distillation column 138 is recycled to stripper 128.

The material withdrawn from the bottom of stripper 128 (i.e. hydrated magnesium-aluminum-silicon mixed metal oxide) is charged to spray dryer 142.

The spray dried hydrated magnesium-aluminum-silicon mixed metal oxide is passed to filter bag house 144 from which gas is exhausted. The solid material retained by the filter bag house 144 is passed to rotary calciner 146 where a magnesium-aluminum-silicon mixed metal oxide agglomerate is produced.

The calcined material is ground in jet mill 148 and conveyed to filter bag house 150. Gas is exhausted from the filter bag house 150, while the retained material is put in drums at product drumming unit 152 for subsequent compaction, sintering, and use.

EXAMPLE 1

For this alkoxide synthesis, a reactor made from a 22 liter glass flask is used. The flask has 3 openings to receive a thermometer and a mixer and to discharge gas produced during the alkoxide synthesis. The opening for discharging gas is provided with a condenser to return condensibles to the reactor and is followed by a gas meter to measure the volume of non-condensible gas produced. The opening for the thermometer has a branch through which reactants can be added to the flask. A resistance heater is positioned beneath the reaction flask to warm the contents of the flask.

In the reaction flask, the following reactants are mixed: 5.556 kilograms of tetraethylorthosilicate, 349.62 grams of aluminum metal, 382.74 grams of magnesium metal, 2.99 grams of iodine, and 450 grams of ethanol. The heater is then turned on to warm the reactants. The reactants are heated to 70° C. An exothermic reaction between the alcohol and metals occurs, causing the temperature to rise to the boiling point of the liquid reactants, which is approximately 78° C. Once the reaction is near completion, the flask contents are allowed to cool, at which time additional alcohol is added to permit further reaction with the remaining metal. This periodic alcohol addition is performed according to the schedule set forth below in Table 1. Periodic alcohol addition in less than stoichiometric quantities required to complete reaction permits better control over the reaction rate.

TABLE 1

| TIME | ALCOHOL ADDED, (GRAMS) | TEMPERATURE AT TIME OF ADDITION (°C.) |
| --- | --- | --- |
| 0 hours | 615 | 70 |
| 18 hours | 585 | 20 |
| 35 hours | 1400 | 20 |
| 39 hours and 10 minutes | 500 | 30 |
| 62 hours and 40 minutes | 1000 | 78 |
| 63 hours and 10 minutes | 104 | N/A (not available) |

As a result of this reaction, 9.845 kilograms of mixed liquid alkoxide are produced. The alkoxide is analyzed by a spectrographic technique and is found to contain the metallic components set forth in Table 2.

TABLE 2

| | |
|---|---|
| Mg | 3.80 wt % |
| Al | 3.49 wt % |
| Si | 9.62 wt % |

A visual inspection of the alkoxide indicates that all of the metal reactants are in solution.

A second reactor is now used to process the alkoxide. The second reactor is a steam jacketed, stainless steel vessel with a volume of 20 gallons. This reactor is provided with a mixer, a thermocouple, an opening to charge reactants, a vapor outlet opening provided with a condenser positioned so that condensate is returned to the reactor, and a bottom outlet to discharge the liquid product.

The 9.845 kilograms of mixed liquid alkoxide are added to the second reactor containing 7.870 kilograms of ethanol. A mixture of 52.31 grams of boric acid and 370 grams of ethanol is then added to second reactor. Next, 47.75 grams of phosphoric acid (85%) mixed with 3.160 kilograms of distilled water and 23.640 kilograms of ethanol are mixed in a tank and then transferred to the second reactor. The second reactor's mixer is operated for 5 minutes to agitate its contents and to effect hydrolysis. The material in the reactor is then allowed to gel and quiescently age for 16 hours. To shear the gel, 20.755 kilograms of distilled water is added to the reactor. The contents of the second reactor are then warmed by operation of the steam jacket and stirred using the mixer to break up the gel into small particles. During this step, the condenser on the outlet of the second reactor which returns condensate to the reactor is shut off, and a downstream condenser is operated to remove condensed alcohol and water from the system. Alcohol and water vapors are continuously removed from the reactor by distillation and replaced with water (Aliquots of water are added to the reactor according to the schedule noted below in Table 3). The net effect of this removal and replacement is to maintain approximately a constant liquid volume.

TABLE 3

| TIME | WATER ADDITION. GRAMS | REACTOR TEMPERATURE °C. |
|---|---|---|
| 0 | 20.775 | |
| 0.5 minutes | 21.540 | 78 |
| 26.5 minutes | 22.460 | 84 |
| 57.5 minutes | 10.895 | 92 |
| 1 hour 14.5 minutes | 10.905 | 93 |
| 1 hour 18.5 minutes | 8,880 | N/A |
| 1 hour 32.5 minutes | 10.960 | 93 |
| 2 hours 21.5 minutes | 21.875 | N/A |
| 4 hours 25.5 minutes | 11.610 | 95 |

The steam for the jacket of the second reactor is then shut off, and the product is drained from the bottom outlet of the second reactor into a plastic drum where it is aged at room temperature for 4 days.

After aging, the material in the plastic drum is transferred back to the second reactor where it is heated for 41 minutes at 100° C. by steam in the reactor jacket to remove any remaining alcohol by distillation. After the steam is shut off, the contents of the second reactor are cooled to 68° C., and 11.210 kilograms of distilled water are added. After two hours and 4 minutes, 57.485 kilograms of hydrated magnesium-aluminum-silicon mixed liquid oxide slurry are removed from the reactor, dried in an oven at 100° C., and ball-milled for 1 hour. The chemical composition of the resultant product is analyzed in an induction coupled argon plasma spectrographic analyzer. The product's composition is shown below in Table 4.

TABLE 4

| | |
|---|---|
| MgO | 14.5 wt % |
| $Al_2O_3$ | 15.3 wt % |
| $SiO_2$ | 30.4 wt % |
| $B_2O_3$ | 0.67 wt % |
| $P_2O_5$ | 0.71 wt % |
| Loss on Ignition | 39.1 wt % |

After ball milling, the resultant product is calcined according to the following schedule: Heating from room temperature to 100° C. in 1 hour; Soaking at 100° C. for 1 hour; Heating from 100° to 700° C. at a rate of 100° C. per hour; Soaking at 700° C. for two hours; and Cooling to room temperature. Following calcination, the product is jet milled to an average particulate size of approximately 4 μ.

EXAMPLE 2

Using a first reactor similar to that utilized in Example 1, 5.555 kilograms of tetraethylorthosilicate, 350.04 grams of aluminum metal, 382.37 grams of magnesium metal, 2.72 grams of iodine, and 1395 grams of ethanol are mixed. This reaction mixture is then heated for several hours, and, when it reaches 70° C., 1.600 kilograms of ethanol are added. Upon continued heating, the reactor contents boil violently, and the exothermic reaction between the alcohol and metals proceeds. When the reactor is at 78° C. after 1 hour and 48 minutes, an additional 800 grams of ethanol are added with another 45 grams added 34 minutes after that. Twenty two hours and 16 minutes later, 1.745 kilograms of ethanol are added. This reaction proceeds until all of the metal reactants are in solution, and an alkoxide is produced. The chemical composition of the alkoxide is then analyzed spectographically and found to have the metallic components shown in Table 5 below.

TABLE 5

| | |
|---|---|
| Mg | 4.28 wt % |
| Al | 3.90 wt % |
| Si | 9.11 wt % |

The 8458.64 grams of alkoxide are then mixed with 10.330 kilograms of ethanol in the second reactor used in Example 1. Next, 51.99 grams of boric acid dissolved in 406.43 grams of ethanol are added to the second reactor. In a separate tank, 48.49 grams of phosphoric acid (85%), 3.30 kilograms of distilled water, and 28.850 kilograms of ethanol are mixed together and then added to the reactor. The contents of the reactor are mixed for 5 minutes and then allowed to set and form a gel. After 20 hours and 30 minutes of setting, 22.675 kilograms of distilled water are added to the reactor, and the mixer is used to shear the gel and break it up into small particles. The composition of the sheared gel is shown in Table 6 below.

TABLE 6

| | |
|---|---|
| MgO | 1.27 wt % |
| $Al_2O_3$ | 1.21 wt % |
| $SiO_2$ | 4.5 wt % |
| $B_2O_3$ | 0.0556 wt % |
| $P_2O_5$ | 0.0491 wt % |

The remainder of the sheared gel is primarily water and alcohol. The steam jacket is then operated to remove alcohol azeotropically from the reactor. During this step, the condensor on the outlet of the second reactor is shut off, and a downstream condensor is operated to remove condensible alcohol and water vapors from the system. Alcohol and water vapors are continuously removed from the reactor by distillation, during which time aliquots of water are added to the reactor in quantities necessary to maintain approximately a constant volume. The schedule of water addition and reactor temperatures are given in Table 7 below.

TABLE 7

| TIME | WATER ADDED, GRAMS | REACTOR TEMPERATURE (°C.) |
|---|---|---|
| 20 hours 30 minutes | 22,675 | N/A |
| 20 hours 48 minutes | 20,895 | N/A |
| 20 hours 53 minutes | 11,680 | 79 |
| 21 hours 4 minutes | 22,705 | 85 |
| 21 hours 22 minutes | 11,190 | 89 |
| 21 hours 29 minutes | 10,955 | 94 |
| 21 hours 44 minutes | 10,615 | 95 |
| 21 hours 54 minutes | 11,285 | 97 |
| 22 hours 4 minutes | 11,540 | N/A |

The steam jacket heater is then shut down, and the resulting material is allowed to age for 4 days. A chemical analysis of the aged slurry product is shown below in Table 8.

TABLE 8

| MgO | 0.60 wt % |
|---|---|
| $Al_2O_3$ | 0.58 wt % |
| $SiO_2$ | 1.0 wt % |
| $B_2O_3$ | 0.0298 wt % |
| $P_2O_5$ | 0.0288 wt % |

After aging is completed, the aged material is heated to 94° C. to effect a final distillation of residual alcohol. During this distillation step, 10.290 kilograms of distilled water are added to the second reactor. After 2 hours of distillation, 62.259 kilograms of hydrated magnesium-aluminum-silicon oxide product are withdrawn from the bottom of the reactor and dried in an oven at 100° C. The chemical analysis of the hydrated magnesium-aluminum-silicon oxide product prior to drying is shown below in Table 9.

TABLE 9

| MgO | 0.67 wt % |
|---|---|
| $Al_2O_3$ | 0.64 wt % |
| $SiO_2$ | 1.23 wt % |
| $B_2O_3$ | 0.028 wt % |
| $P_2O_5$ | 0.030 wt % |

A 1.265 kg sample of the dry product is then ball milled for 4 hours. After ball milling, the sample was chemically analyzed and found to have the composition shown below in Table 10.

TABLE 10

| MgO | 16.4 wt % |
|---|---|
| $Al_2O_3$ | 17.3 wt % |
| $SiO_2$ | 30.7 wt % |
| $B_2O_3$ | 0.71 wt % |
| $P_2O_5$ | 0.77 wt % |

An x-ray diffraction pattern of the sample showed that it was amorphous. According to a scanning electron micrograph of the powder, the agglomerates are comprised of sub-micron particles.

A 103.23 gram sample of dried, unmilled hydrated magnesium-aluminum-silicon oxide is calcined in an oven according to the following schedule: Heating from room temperature to 700° C. at a rate of 100° C. per hour; Soaking at 700° C. for 4 hours; Heating to 800° C. over the course of an hour; Soaking at 800° C. for 4 hours; and Cooling to room temperature.

An x-ray diffraction pattern of the product indicates that it is amorphous. An infra-red absorption pattern indicates that the sample is amorphous cordierite glass.

A 46.00 gram powder sample of calcined material produced according to the previous paragraph is again calcined according to the following schedule: Heating from room temperature to 800° C. at a rate of 200° C. per hour; Heating to 1000° C. over a 2 hour period; Soaking at 1000° C. for 2 hours; and Cooling to room temperature. An x-ray diffraction pattern of the sample indicates that the sample is high (hexagonal) cordierite ($2Mgo.2Al_2O_3.5SiO_2$). The infra-red absorption pattern indicates that the sample is highly crystalline.

A 2.39 kg portion of the unmilled dried powder was ball milled for 2 hours, followed by calcination according to the following schedule: Heating from room temperature to 700° C. at 100° C. per hour; Soaking at 700° C. for 18 hours; and Cooling. A chemical analysis of the calcined powder is given in Table 11 below.

TABLE 11

| MgO | 21.0 wt % |
|---|---|
| $Al_2O_3$ | 22.0 wt % |
| $SiO_2$ | 38.9 wt % |
| $B_2O_3$ | 0.96 wt % |
| $P_2O_5$ | 0.98 wt % |
| Loss on Ignition | 15.9 wt % |

An x-ray diffraction pattern indicates that the powder is amorphous.

Four disks of the calcined powder are prepared by pressing the powder in a 1 ⅛ inch die at 30,000 psi. The green density is measured to be 1.16 grams per cubic centimeter. After pressing, the disks are heated according to the following schedule to effect sintering: Heating from room temperature to 700° C. at a rate of 200° C. per hour; Heating from 700° to 850° C. at a rate of 100° C. per hour; Soaking at 850° C. for four hours; and Cooling. The density is measured to be 2.43 grams per cubic centimeter or approximately 95% of theoretical density.

EXAMPLE 3

In a first reactor like that used in Example 1, 5.570 kilograms of tetraethylorthosilicate, 1.79 grams of iodine, 354.76 grams of aluminum metal, 381.78 grams of magnesium metal, and 1.075 kilograms of ethanol are mixed and heated to 80° C. After about 17 hours, ethanol is added to the reactor which is operating at 50° C. according to Table 12 below.

TABLE 12

| TIME | ETHANOL ADDITION (GRAMS) |
|---|---|
| 0 | 235 |
| 1 hour 42 minutes | 265 |
| 5 hours 37 minutes | 855 |
| 23 hours 42 minutes | 610 |
| 31 hours 12 minutes | 2550 |

As a result of this reaction, 11.610 kilograms of magnesium-aluminum-silicon mixed liquid alkoxide are produced. The product is analyzed by spectrographic techniques and found to have the composition shown below in Table 13.

TABLE 13

| Mg | 5.48 wt % |
|---|---|
| Al | 5.73 wt % |
| Si | 14.20 wt % |

No visible metal reactants are left after the reaction is completed.

Using a second reactor like that used in Example 1, 10.0186 kilograms of the alkoxide are mixed with 6610 kilograms of ethanol and heated to 54° C. A mixture of 46.80 grams of boric acid and 200.12 grams of ethanol are then added to the reactor. In a transfer tank similar to that used in Example 1, 42.85 grams of phosphoric acid (85%), 2792.81 grams of distilled water, and 18.210 kilograms of ethanol are mixed. With the reactor temperature at 58° C., the contents of the transfer tank are mixed with that of the second reactor. The material in the second reactor is then heated to 78° C. so that it begins to gel. The gel is allowed to age for 2 hours with only the gel in the middle of the reactor being agitated. After 2 hours of aging, 8310.96 grams of distilled water is added to the second reactor. The material in the second reactor is then aged for 1 hour.

After aging is completed, the contents of the reactor are heated to distill ethanol as described in earlier Examples 1 and 2.

During distilling, water is added according to the schedule shown below in Table 14.

TABLE 14

| TIME | WATER ADDED GRAMS | REACTOR TEMPERATURE (°C.) |
|---|---|---|
| 20 minutes | 10.175 | 78 |
| 27 minutes | 10.345 | 80 |
| 37 minutes | 11.020 | 84 |
| 46 minutes | 11.145 | 87 |
| 57 minutes | 11.485 | 93 |
| 1 hour 9 minutes | 11.500 | 97 |

The reactor temperature is then raised to 100° C. and maintained at that temperature for 15 minutes. The removal of ethanol and water and the addition of water are then stopped, and 63142.49 grams of material are removed from the bottom of the reactor. A 277.49 gram portion of the product is retained for analysis. Table 15 below shows the composition of the product.

TABLE 15

| MgO | 0.83 wt % |
|---|---|
| $Al_2O_3$ | 0.82 wt % |
| $SiO_2$ | 1.7 wt % |
| $B_2O_3$ | 0.0375 wt % |
| $P_2O_5$ | 0.0388 wt % |
| $H_2O$ | 96.8 wt % |

The 62865 gram remainder of the product is dried in an oven and analyzed. Table 16 below shows the composition of the product.

TABLE 16

| MgO | 11.9 wt % |
|---|---|
| $Al_2O_3$ | 12.7 wt % |
| $SiO_2$ | 25.9 wt % |
| $B_2O_3$ | .52 wt % |
| $P_2O_5$ | .55 wt % |
| Loss on Ignition | 48.7 wt % |

Half of the resulting dry powder is calcined after ball milling for 2 hours according to the following schedule: Heating from room temperature to 500° C. at a rate of 50° C. per hour; Soaking at 500° C. for 2 hours; Heating from 500° C. to 700° C. at a rate of 50° C. per hour; Soaking at 700° C. for 4 hours; and Cooling to room temperature. The calcined powder is chemically analyzed and found to have the composition shown below in Table 17.

TABLE 17

| MgO | 18.3 wt % |
|---|---|
| $Al_2O_3$ | 19.5 wt % |
| $SiO_2$ | 39.9 wt % |
| $B_2O_3$ | 0.78 wt % |
| $P_2O_5$ | 0.83 wt % |
| Loss on Ignition | 20.6 wt % |

An x-ray diffraction pattern of the calcined powder indicates that the sample is amorphous.

The other half of the dried material is ball milled for 3 hours and then calcined. Calcination is effected according to the following schedule: Heating from room temperature to 500° C. at a rate of 50° C. per hour; Soaking at 500° C. for 2 hours; Raising the temperature from 500° C. to 700° C. at 50° C. per hour; Soaking at 700° C. for 4 hours; and Cooling to room temperature. An x-ray diffraction pattern indicates that the powder is amorphous.

The calcined powder is mixed together and then jet milled. The jet milled powder is then pressed into 1 ⅛" inch diameter disks with a pressure of 30,000 psi. The disks are then sintered according to the following schedule: Heating from room temperature to 950° C. at a rate of 100° C.; Soaking at 950° C. for 4 hours; and Cooling to room temperature. The density of the disk is measured to be 2.50 grams per cubic centimeter.

EXAMPLE 4

Powder is prepared substantially according to the procedure described in Example 1. After calcining to 700° C., and jet milling, the powder is analyzed and found to have the composition shown below in Table 18.

TABLE 18

| MgO | 20.3 wt % |
|---|---|
| $Al_2O_3$ | 21.6 wt % |
| $SiO_2$ | 40.7 wt % |
| $B_2O_3$ | 0.83 wt % |
| $P_2O_5$ | 0.88 wt % |
| LOI | 15.9 wt % |

An x-ray diffraction pattern indicates that it is amorphous. Disks of 1 ⅛" diameter, each weighing 3 grams, are pressed using a pressure of 30,000 psi. The green densities of the disks are given below in Table 19.

TABLE 19

| DISK # | GREEN DENSITY GRAMS PER CUBIC CENTIMETER |
|---|---|
| 1 | 1.25 |
| 2 | 1.19 |
| 3 | 1.22 |
| 4 | 1.24 |
| 5 | 1.24 |
| 6 | 1.20 |

Disks 1 and 2 are sintered at 875° C. according to the following schedule: Heating from room temperature to 700° C. at 150° C. per hour; Heating from 700° to 875° C. at 100° C. per hour; Soaking at 875° C. for 2 hours;

and Cooling. An x-ray diffraction of a monolithic part of one disk indicates that it is comprised of high (hexagonal) cordierite. The other disk is ground into a powder. The ground material is analyzed and found to have an infra-red absorption pattern which indicates that it is crystalline cordierite. An x-ray diffraction pattern indicates that it is high (hexagonal) cordierite. The density is measured to be 2.50 grams per cubic centimeter.

Disks 3 and 4 are sintered to 850° C. according to the following schedule: Heating from room temperature to 700° C. at 150° C. per hour; Heating from 700° to 850° C. at 100° C. per hour; Soaking at 850° C. for two hours; and Cooling. An x-ray diffraction pattern of a monolithic portion of a disk indicates that it is amorphous. The disks are re-calcined to 825° C. at 100° C. per hour, and allowed to cool. An x-ray diffraction pattern of a ground portion of the disk indicates that it is amorphous. An infra-red absorption pattern indicates that the powder is amorphous. Density is measured to be 2.44 grams per cubic centimeter.

Disks 5 and 6 are sintered to 825° C. according to the following schedule: Increasing the temperature from room temperature to 825° C. at 100° C. per hour; Soaking at 825° C. for two hours; and Cooling. An x-ray diffraction pattern of each disk indicates that it is amorphous.

EXAMPLE 5

263 grams of calcined, milled powder prepared substantially according to the procedure outlined in Example 1 is re-calcined to 800° C. according to the following schedule: Heating from room temperature to 500° C. at 100° C. per hour; Soaking at 500° C. for 3 hours; Heating from 500° to 800° C. per hour; Soaking at 800° C. for 2 hours; and Cooling. The powder is dry ball milled for 1 hour and pressed into a 1 ⅛" diameter, 2 gram disk at 30,000 psi. The disk is sintered at 850° C. according to the following schedule: Heating from room temperature to 700° C. at 100° C. per hour; Soaking at 700° C. for 1 hour; Heating from 700° to 825° C. at 100° C. per hour; Soaking at 825° C. for 3 hours; Heating from 825° to 850° C. at 100° C. per hour; Soaking at 850° C. for 4 hours; and Cooling. The density of the disk is measured to be 2.55 grams per cubic centimeter, while an infra-red absorption pattern indicates that it is amorphous.

Three disks prepared as described above and sintered to 850° C. are re-sintered to 875° C. according to the following schedule: Heating from room temperature to 875° C. at 150° C. per hour; Soaking at 875° C. for 2 hours; and Cooling. An x-ray diffraction pattern indicates that the disks are high (hexagonal) cordierite.

Although the invention has been described in detail for the purpose of illustration, it is understood that such detail is solely for that purpose, and variations can be made therein by those skilled in the art without departing from the spirit and scope of the invention.

What is claimed:

1. A ceramic powder consisting essentially of agglomerates of fine sub-micron size hydrated metal oxide particles of magnesium-aluminum-silicon which form hexagonal cordierite at substantially full density at a sintering temperature of between 825° C. and 875° C.

2. A ceramic powder consisting essentially of agglomerates of fine sub-micron size hydrated metal oxide particles of magnesium-aluminum-silicon which form hexagonal cordierite at substantially full density at a sintering temperature of between 825° C. and 875° C. and a sintering aid selected from the group consisting of an oxide of boron and an oxide of phosphorus.

3. A ceramic powder as defined in claim 2 wherein $B_2O_3$ and $P_2O_5$ are present in amounts below about 1 weight percent respectively.

* * * * *